United States Patent

Douglas et al.

[11] 3,931,188
[45] Jan. 6, 1976

[54] 3-HYDROXY-5,6-BENZOMORPHINAN DERIVATIVES

[75] Inventors: James L. Douglas, Montreal; Jacques Meunier, LaSalle; Marcel Menard, Candiac, all of Canada

[73] Assignee: Bristol-Myers Company, New York, N.Y.

[22] Filed: May 6, 1974

[21] Appl. No.: 467,339

[52] U.S. Cl. ....... 260/285; 260/283 SY; 260/289 R; 260/286 A; 260/348 A; 260/570.5 CA; 424/260
[51] Int. Cl.² ............. C07D 221/22; C07D 221/28; A61K 31/485
[58] Field of Search .............................. 260/243 C

[56] References Cited
UNITED STATES PATENTS
3,329,682  7/1967  Bentley .................. 260/285

FOREIGN PATENTS OR APPLICATIONS
45-25300  8/1970  Japan ................... 260/285

OTHER PUBLICATIONS
Bentley et al., Proc. Chemical Soc. (London), p. 220, (1963).

Primary Examiner—Donald G. Daus
Assistant Examiner—Diana G. Rivers
Attorney, Agent, or Firm—Robert E. Havranek

[57] ABSTRACT

Compounds having the formula

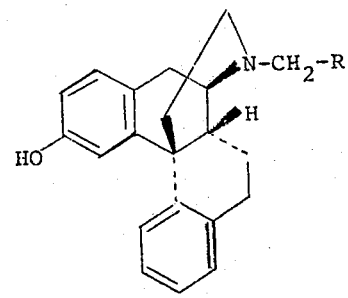

in which R is cyclopropyl or cyclobutyl have been designated 3-hydroxy-17-substituted-5,6-benzomorphinans. The compounds possess potent narcotic agonist and/or antagonist activity. In particular, the compounds 3-hydroxy-17-cyclopropylmethyl-5,6-benzomorphinan and 3-hydroxy-17-cyclobutylmethyl-5,6-benzomorphinan have been found to possess both activities. These compounds are prepared by total synthesis and are not derived from opium alkaloids.

9 Claims, No Drawings

3-HYDROXY-5,6-BENZOMORPHINAN DERIVATIVES

BACKGROUND OF THE INVENTION

1. Field of the Invention

This invention embodies new and novel compounds useful as analgesics and/or narcotic antagonists and a new and novel total synthesis for their preparation.

2. Description of the Prior Art

A. The synthesis of N-cyclopropylmethyl-3-hydroxymorphinan and N-cyclobutylmethyl-3-hydroxymorphinan is reported in *Chemical Abstracts*, 63, columns 18050 – 18051 (abstract of Belgian Pat. No. 644,679). These compounds are reported to be analgesics and antagonists to meperidine.

B. The synthesis of 3-carboxamido-1,2,3,4,5,6-hexahydro-2,6-methano-3-benzazocin-8-ol, having the formula

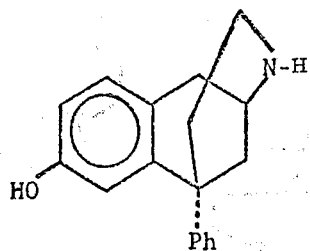

is described by F. B. Block and F. H. Clarke in *J. Med. Chem.*, 12, pages 845 – 847 (1969). This paper reports the compound to be an orally effective analgetic and to have an unusual freedom from physical dependence capacity in the monkey.

C. The synthesis of various 6,7-benzomorphan derivatives and their analgetic activity is reported by K. Kanematsu, M. Takedo, A. Jacobson and E. May in *J. Med. Chem.*, 12, pages 405 – 408 (1968) and by S. Fullerton, E. May and E. Becker in *J. Org. Chem.*, 27, pages 2144 – 2147 (1962).

SUMMARY OF THE INVENTION

Compounds having the formula

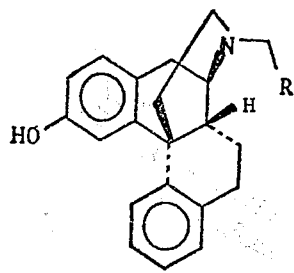

wherein R is selected from the group comprising

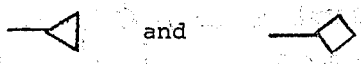

or pharmaceutically acceptable acid addition salts thereof are analgetic agents, narcotic antagonists or intermediates in the preparation of such agents.

DISCLOSURE OF THE INVENTION

This invention relates to new and novel 3-hydroxy-17-substituted-5,6-benzomorphinan derivatives having the formula

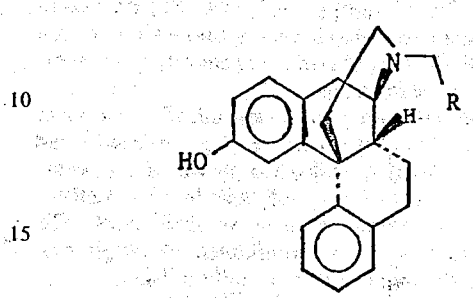

wherein $R^1$ is selected from the group comprising

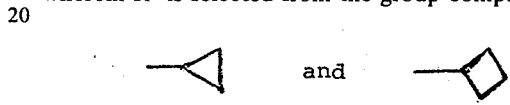

or pharmaceutically acceptable acid addition salts thereof.

Drug abuse by thrill-seeking youth or by people looking for an escape from the realities of every day life has become more and more commonplace in our present society. One class of widely abused drugs are the narcotic analgetics such as codeine, morphine, meperidine, etc. It is because of the high addictive potential of these agents that much time and money are being expended by the pharmaceutical industry and by governments to try and discover and develop new non-addicting analgetics and/or narcotic antagonists.

It was, therefore, an object of the present invention to find new and novel compounds that have these characteristics.

It was further an object of the present invention to develop a method of synthesis that would not be dependent upon opium alkaloids as starting materials and yet would be commercially feasible.

The objectives of the present invention have been achieved by the provision of 3-hydroxy-17-substituted-5,6-benzomorphinan derivatives and by their total synthesis from the readily available starting material 1-tetralone or 3,4-dihydro-1-methyl napthalene.

The compounds of the instant invention have the basic 5,6-benzomorphinan nucleus which is numbered and represented by the following plane formula:

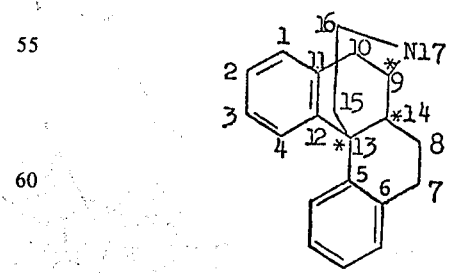

Although there are three asymmetric carbons (asterisks) in the morphinan molecule, only two diastereoisomeric (racemic) forms are possible, because the iminoethano system, attached to position 9 and 13, is geometrically contained to a cis-(1,3-diaxial)-fusion. These racemates can, therefore, differ only in the configuration of carbon 14. The only variable will be the cis and trans relationship between the 5 (13) and 8 (14) bonds. (Analgetics, Ed. George de Stevens, Academic Press, New York, p. 137 (1965). The compounds claimed herein have a cis relationship between the 5(13) and 8(14) bonds and are, therefore, morphinans and not isomorphinans.

The present invention embodies all of the optical isomers. The optical isomers can be separated and isolated by fractional crystallization of the diastereoisomeric salts formed, for instance, with d- or l- tartaric acid or D-(+)-α-bromocamphor sulfonic acid. The levorotatory isomers of the compounds of the present invention are the most preferred embodiments.

The term "pharmaceutically acceptable acid addition salt" is defined to include all those inorganic and organic acid salts of the compounds of the instant invention, which salts are commonly used to produce nontoxic salts of medicinal agents containing amine functions. Illustrative examples would be those salts formed by mixing the compounds of formula I with hydrochloric, sulfuric, nitric, phosphoric, phosphorous, hydrobromic, maleic, malic, ascorbic, citric or tartaric, pamoic, lauric, stearic, palmitic, oleic, myristic, lauryl sulfuric, napthalinesulfonic, linoleic or linolenic acid, and the like.

The compounds of the instant invention are prepared by a total synthesis comprising the steps outlined in the following chart:

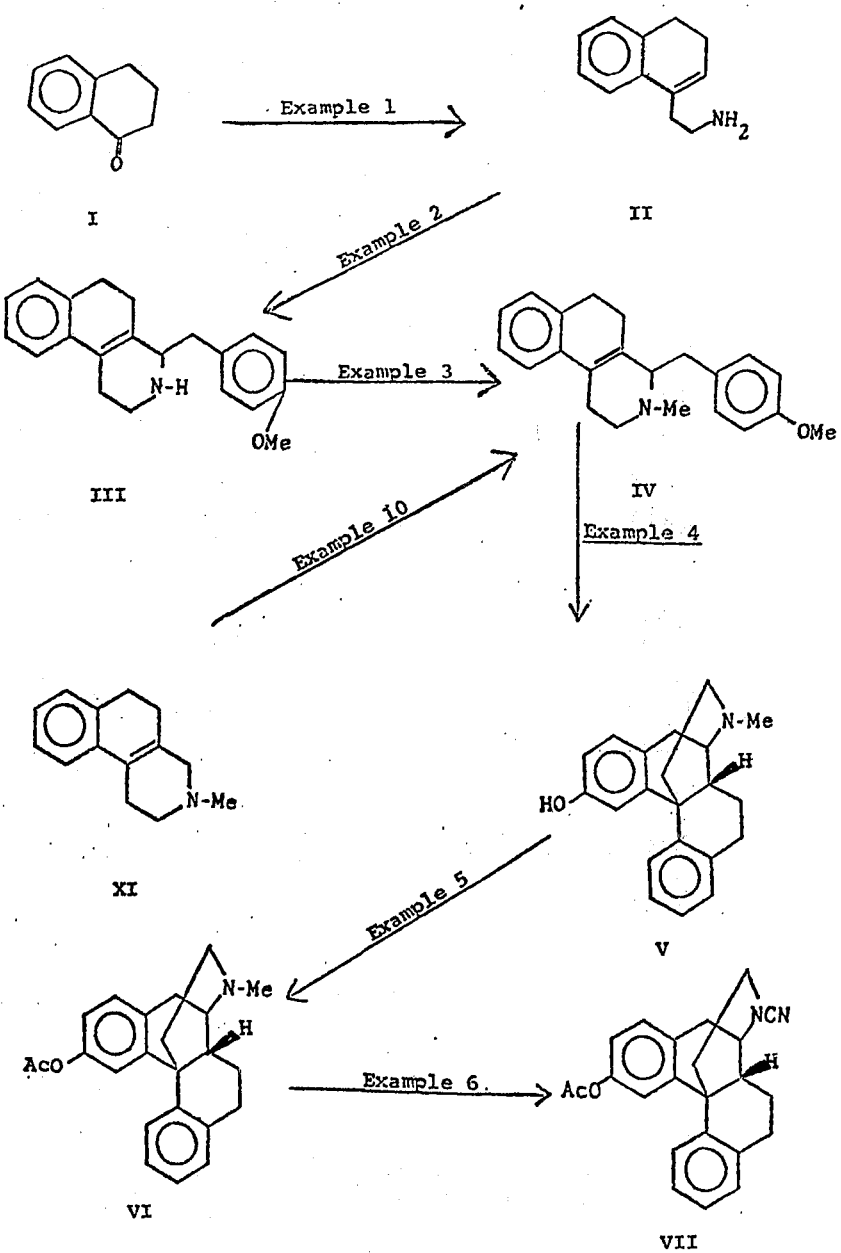

Chart

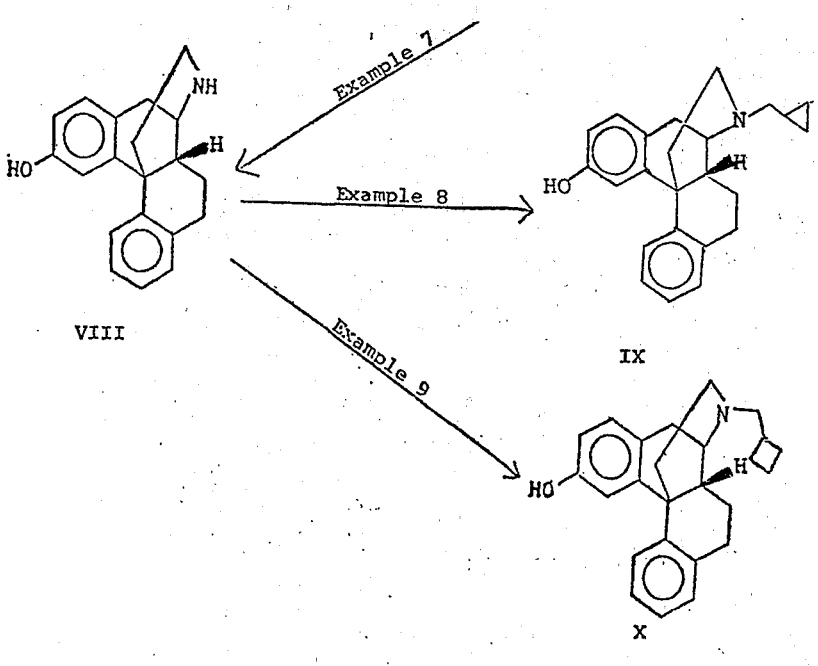

The processes for the preparation of the compounds of this invention are new and novel. In accordance with this invention, the compound 4-(4-methoxybenzyl)-3-methyl-1,2,3,4,5,6-hexahydrobenz[f]isoquinoline (IV) which may be prepared by two alternate processes as described hereinafter in Examples 1 – 3 and Example 10, is cyclized by heating it in the presence of hydrobromic acid to form 3-hydroxy-17-methyl-5,6-benzomorphinan (V). Compound V is then converted to its acetate ester (VI), by treating it with acetic acid, the ester VI is N-demethylated by treating it with cyanogen bromide to give 3-acetoxy-17-cyano-5,6-benzomorphinan (VII) and this compound is reduced by treatment with lithium aluminum hydride to form 3-hydroxy-5,6-benzomorphinan (VIII). Compound VIII is then treated with cyclopropylcarbonyl chloride or cyclobutylcarbonyl chloride, followed by reduction to obtain 3-hydroxy-17-cyclopropylmethyl-5,6-benzomorphinan or 3-hydroxy-17-cyclobutylmethyl-5,6-benzomorphinan.

It is well known in the narcotic analgesic prior art that it is possible for some compounds to possess both agonist and antagonist properties. An agonist is a compound that imitates a narcotic analgesic and possesses analgetic qualities. An antagonist is a compound that counteracts the analgetic and euphoric properties of a narcotic analgesic. It is possible for a compound to have both properties. A good example of such a compound is cyclazocine.

In vivo testing was conducted on the hydrochloride salts of compounds IX and X to determine their agonist and/or antagonist properties. The following table represents the results of the experiments. The figures reported are the number of milligrams/kilogram of body weight of compound that produced an agonist or antagonist effect in 50 percent of the mice and rats so tested ($ED_{50}$) when administered subcutaneously.

TABLE

| | $ED_{50}$(mg./kg.) | | |
|---|---|---|---|
| | Analgesic Activity | Antagonist Activity | |
| Test Compound | Mouse Phenylquinone Writhing[1] | Oxymorphone Straub Tail[2] | Morphine Antagonist Rat Tail Flick[3] |
| dl-IX | ≈4.5 | ≈40 | 2.3 |
| dl-X | ≈4.5 | >40 | not done |
| Pentazocine | 3.7 | 12 | 12.2 |

[1] A 50 percent reduction in number of phenylquinone induced writhings [Siegmumd, E.A., et al., Proc. Soc. Biol. & Med 95, p. 729 (1957)].
[2] Antagonism of Straub Tail induced by oxymorphone (2 mg./kg. s.c.) in 50 percent of mice.
[3] A 50 percent reduction of analgesic effect induced by morphine (15 mg./kg. s.c.) as measured by the rat tail flick procedure. [Harris L.S., and Person, A.K., J. Pharmacol. & Exptl. Therap. 143, p. 141, (1964)].

It is apparent from the testing that compounds IX and X have about the same analgesic potency as pentazocine. Although compound IX had little antagonist activity, compound X was approximately 5 times more active as an antagonist in the rat than was pentazocine. Behavioral studies in the dog showed both compounds IX and X to be free of side effects at a subcutaneous dose of 2 mg./kg. The normal parenteral dosage of the compounds of this invention in adult humans is about 0.25 to 16 mg. three to four times a day.

EXPERIMENTAL SECTION

EXAMPLE 1

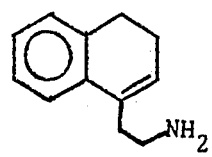

4-(2-Aminoethyl)-1,2-dihydronaphthalene (II)

A solution of 107 g. (1.67 mole) of n-butyl lithium in 288 ml. of hexane was cooled to −78°C. and 240 ml. of tetrahydrofuran was added. A solution of 24 ml. (0.46 mole) of acetonitrile in 360 ml. of tetrahydrofuran was added over 20 minutes. After stirring for 1 hour at −78°C., a solution of 58.5 g. (0.40 mole) of 1-tetralone in 400 ml. of tetrahydrofuran was added over 15 minutes. The cold bath was removed and stirring was continued for another 15 minutes. Lithium aluminum hydride, 18 g. (0.48 mole), was added and the mixture was stirred at 24°C. for 3 hours. After cooling to 0°C., 18 ml. of water was added cautiously, followed by 13.5 ml. of 20% by weight of an aqueous solution of NaOH and 63 ml. of water. After stirring at 24°C. for 15 minutes, the inorganic salts were filtered off. The ether solution was extracted twice with 500 ml. portions and once with a 100 ml. portion of 10% by weight aqueous HCl. The aqueous layers were made basic by the addition of 25% by weight of NaOH in water and extracted three times with 500 ml. portions of ether to give a yellow oil. A benzene solution of the oil was saturated with HCl gas and refluxed under a water separator until water ceased to pass over. After cooling to 10°C., the crystalline hydrochloride salt of the product was collected in approximately 70 percent overall yield.

EXAMPLE 2

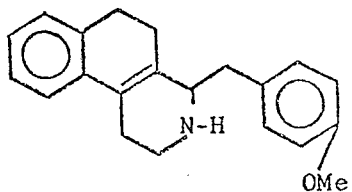

4-(4-methoxybenzyl)-1,2,3,4,5,6-hexahydrobenz[f]isoquinoline (III)

Ethanol free sodium ethoxide was mixed with 200 ml. of toluene and cooled to 0°C. A solution of p-methoxybenzaldehyde, 56.0 g. (0.412 mole), and ethyl chloroacetate, 50.5 g. (0.412 mole), in 200 ml. of toluene was added at such a rate that the temperature remained below 10°C. After stirring at 24°C. for 16 hours, the mixture was washed twice with 400 ml. portions of water and dried over anhydrous sodium sulfate. The solvent was evaporated to give a yellow liquid of about 80% purity (81.2 g.). The liquid solidified on standing at 5°C. and was further purified by washing with a small volume of cold ethanol to give pale yellow crystals of ethyl 3-(4-methoxyphenyl)-2,3-epoxypropionate having a melting point of between 40° and 43°C.

A mixture 28.4 g. (0.138 mole) of the hydrochloride salt of 2-aminoethyl)-1,2-dihydronaphthalene (II) in water (800 ml.) was acidified to pH 3 by the addition of hydrochloric acid. The resulting mixture was heated under reflux under a nitrogen atmosphere and with vigorous stirring, a solution of 38.0 g. (0.172 mole) of ethyl 3-(4-methoxyphenyl)-2,3-epoxypropionate in 200 ml. of ethanol was added dropwise over a period of 8 hours. Reflux was continued for 16 hours, then 300 ml. of concentrated hydrochloric acid was added. After a further 4 hours under reflux, the mixture was allowed to cool, and benzene (800 ml.), hexane (200 ml.) and methanol (200 ml.) were added, the mixture was shaken and the aqueous layer separated. The aqueous layer was basic and extracted with methylene chloride to give a 56 percent yield of product (III). The nuclear magnetic resonance spectrum of the product was consistent with the structure.

EXAMPLE 3

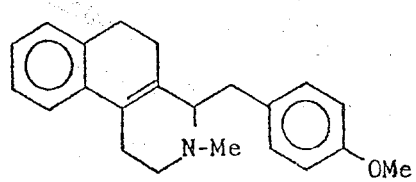

4-(4-Methoxybenzyl)-3-methyl-1,2,3,4,5,6-hexahydrobenz[f]isoquinoline (IV)

A solution of 85% formic acid, 1.30 g., and 37% formaldehyde, 2.16 g., was added slowly, with cooling, to 3.1 g. (10 mole) of 4-(4-methoxybenzyl)-1,2,3,4,5,6,-hexahydrobenz[f]isoquinoline (III). The mixture was heated gently until $CO_2$ evolution ceased and was then heated under reflux for 5 hours. On cooling, 20 ml. of a 10% by weight aqueous solution of NaOH was added and the mixture was extracted with methylene chloride to give a yellow oil. This oil was purified via its picrate salt as follows:

The crude product (57.9 g.) was dissolved in 250 ml. of hot ethanol and a solution of picric acid (50 g.) in 250 ml. of hot ethanol was added with vigorous stirring. After cooling to room temperature, the crude, crystalline picrate salt was filtered off. The picrate salt was stirred vigorously with 1 l. of refluxing acetone, and the mixture was concentrated to 300 ml. On cooling to room temperature, the yellow picrate salt having a melting point of 210° – 212°C. (with decomposition) was collected. The picrate salt was decomposed by mixing with 15 l. of 1% by weight aqueous NaOH and extracting first with 2 l. then with 1 l. of methylene chloride. The combined extracts were washed with 1 l. of 1% by weight aqueous sodium hydroxide, dried, treated with charcoal and evaporated to give 22.9 g. of product (IV) as a yellow-brown solid (42% yield) having a melting point of 210° – 212°C. (with decomposition). The nuclear magnetic resonance spectrum was consistent with the structure.

EXAMPLE 4

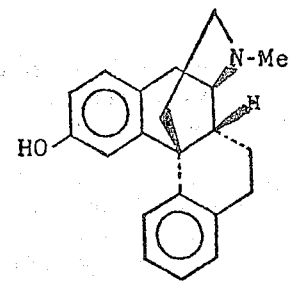

3-Hydroxy-17-methyl-5,6-benzomorphinan(V)

A mixture of 10 g. (31 mmole) of 4-(4-methoxybenzyl)-3-methyl-1,2,3,4,5,6-hexahydrobenz[f]isoquinoline (IV) and 100 ml. of 48% by weight of aqueous HBr was heated under a nitrogen atmosphere at 135° – 140°C. for 10 days. On cooling, the mixture was poured into 200 ml. of ice water, which had been made basic with concentrated $NH_4OH$. The mixture was then extracted with chloroform to give the crude product. The crude product was recrystallized from a mixture of benzene and ethanol. This procedure yielded 4.66 g. of crystals (49%) having a melting point of 243° – 245°C. (with decomposition). The product (V) had a nuclear magnetic resonance spectrum which was consistent with the structure.

EXAMPLE 5

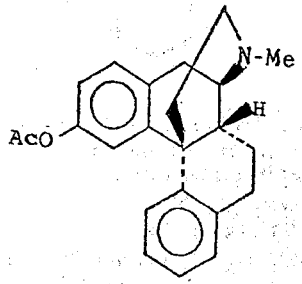

3-Acetoxy-17-methyl-5,6-benzomorphinan (VI)

A solution of 6.1 g. (20 mmole) of 3-hydroxy-17-methyl-5,6-benzomorphinan (V) in 30 ml. of acetic anhydride was heated at 100°C. for 45 minutes. On cooling, the solution was poured into 70 ml. of water at 0°C., stirred for 5 minutes, then made basic by the addition of a slight excess of a 45% by weight aqueous potassium hydroxide solution while cooling in ice. The resulting mixture was extracted with methylene chloride to give 6.9 g. of product (VI) as a pale yellow oil. The infrared and nuclear magnetic resonance spectra were consistent with the structure.

EXAMPLE 6

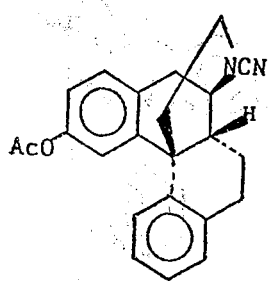

3-Acetoxy-17-cyano-5,6-benzomorphinan (VII)

A solution of 6.8 g. (19.6 mmole) of 3-acetoxy-17-methyl-5,6-benzomorphinan (VI) in 36 ml. of chloroform was mixed with a solution of 2.5 g. (24 mmole) of cyanogen bromide in 30 ml. of chloroform. The resulting solution was heated under reflux for 3 hours. The solvent was evaporated to give 7.5 g. of product (VII) in the form of a brown foam. The infra red and nuclear magnetic resonance spectra were consistent with the structure.

EXAMPLE 7

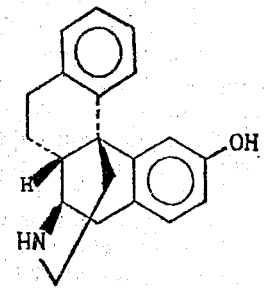

3-Hydroxy-5,6-benzomorphinan (VIII)

A solution of 7.4 g. (20 mmole) of the crude product from Example 6 (VII) in 180 ml. of tetrahydrofuran was added over 5 minutes to a stirred solution of lithium aluminum hydride in 60 ml. of tetrahydrofuran under a nitrogen atmosphere. The stirred mixture was heated under reflux for 16 hours. The heating source was removed and 42 ml. of saturated aqueous sodium chloride was added over a period of 20 minutes. The vigorously stirred mixture was heated under reflux for 1 hour. On cooling, the resultant precipitate was filtered off and the solvent evaporated to give 5.9 g. of product in the form of a yellow solid. The product was recrystallized from methanol to give cyrstals (VIII) having a melting point of 301° – 304°C. (with decomposition). The infra red and nuclear magnetic resonance spectra were consistent with the structure.

EXAMPLE 8

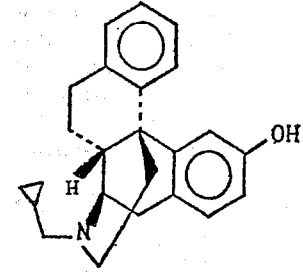

3-Hydroxy-17-cyclopropylmethyl-5,6-benzomorphinan (IX)

A solution of 4.2 g. (40 mmole) of cyclopropylcarbonyl chloride in 20 ml. of methylene chloride was added over 10 minutes to a slurry of 5.4 g. (18.5 mmole) of 3-hydroxy-5,6-benzomorphinan (VIII) and 7.0 ml. (40 mmole) of pyridine in 30 ml. of methylene chloride. After stirring at 24°C. for 30 minutes, the solution was washed successively with water, a 10% by weight aqueous solution of NaHCO$_3$, 10% by weight aqueous hydrochloric acid, and water. The solvent was then evaporated to give 6.4 g. of a crude ester amide having the formula

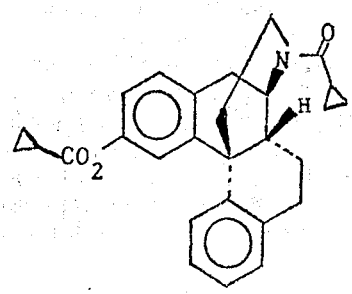

as a yellow foam. A solution of 6.4 g. (15 mmole) of this product in 100 ml. of tetrahydrofuran was added over 10 minutes to a slurry of 3.5 g. (92 mmole) of lithium aluminum hydride in 30 ml. of tetrahydrofuran. After heating under reflux for 1 hour and cooling, 18.5 ml. of a saturated aqueous solution of NaCl was added dropwise. Tetrahydrofuran (30 ml.) was added and the mixture was heated under reflux for 30 minutes. On cooling, the inorganic salts were filtered off and the solvent was evaporated to give the crude product. The product was purified by trituration with a mixture of benzene and ethanol to yield 2.51 g. (49%) of an almost colorless powder (IX), which had a melting point of 263° – 265°C. The infra red and nuclear magnetic resonance spectra were consistent with the structure.

EXAMPLE 9

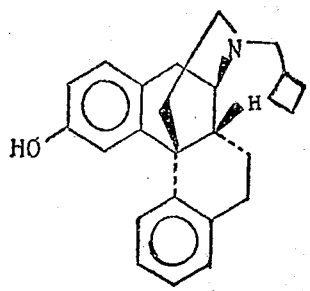

3-Hydroxy-17-cyclobutylmethyl-5,6-benzomorphinan
(X)

The procedure of Example 8 was repeated except that 4.8 g. (40 mmole) of cyclobutylcarbonyl chloride was substituted for the cyclopropylcarbonyl chloride of that example. The crude product was recrystallized from a mixture of dioxane and water. The product (X) had a melting point of 224° – 225°C. and a nuclear magnetic resonance spectrum which was consistent with the structure.

Anal. calc'd for $C_{25}H_{29}NO \cdot \frac{1}{2}H_2O$: C, 81.48; H, 8.21; N, 3.80. Found: C, 81.63; H, 8.27; N, 3.80.

EXAMPLE 10

Alternative method for the preparation of 4-(4-methoxybenzyl)-3-methyl-1,2,3,4,5,6-hexahydrobenz[f]isoquinoline (IV).

A mixture of 86 g. (0.60 mole) of 3,4-dihydro-1-methyl naphthalene, 200 g. (2.4 mole) of a 37% by weight aqueous formaldehyde solution and 100 ml. of glacial acetic acid was stirred vigorously at 60° – 65°C. for ½ hour. There was then added 81 g. (1.4 mole) of monomethylamine hydrochloride in small portions while keeping the temperature at 70°C. After the addition, the mixture was stirred for 3 hours at 70°C., then diluted with 200 ml. of water at 0°C., washed 5 times with 100 ml. portions of ether, made basic with 50% by weight aqueous sodium hydroxide solution and extracted 5 times with 100 ml. portions of ether. Drying and concentration of the ether extracts gave 116 g. of crude intermediate as a yellow oil. The intermediate was dissolved in 100 ml. of concentrated hydrochloric acid and heated under reflux for 2 hours. On cooling, the solution was washed twice with 100 ml. portions of ether, made basic with 50% by weight aqueous sodium hydroxide and extracted 5 times with 100 ml. portions of ether. Drying and concentration of the ether extracts gave 99.5 g. of an oil which was purified by distillation to provide 51.5 g. (51% yield) of an amine in the form of a viscous oil having the structure

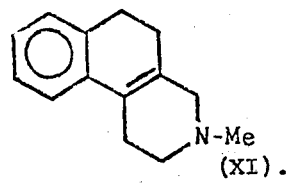

The hydrochloride salt of this amine was recrystallized from a mixture of ethanol and ether to give a solid having a melting point of 208° – 209°C.

Anal. calc'd. for $C_{14}H_{17}N \cdot HCl$: C, 71.32; H, 7.70; N, 5.94. Found: C, 71.18; H, 7.68; N, 6.00.

A solution of 26.7 g. (170 mmole) of anisyl chloride and the above amine (XI) in 100 ml. of acetone was maintained at 0°C. for 1 hour, then at 24°C. for ½ hour. The solvent was evaporated to give a foam. The powdered foam was suspended in 300 ml. of ether and, with stirring, a solution of 220 ml. of 2.2 M phenyl lithium in 40 ml. of ether and 40 ml. of benzene was added at such a rate that reflux was maintained. After a further ½ hour of cooling to 24°C., the reaction mixture was cooled to 0°C., then added to 550 ml. of ice water. This was extracted with ether in the usual manner to give the crude product as an oil. The oil was mixed with 260 ml. of n-hexane and 260 ml. of 3N HCl and enough methanol was added to bring the oily hydrochloride salt into solution. After separation, the aqueous layer was made basic with 25% by weight aqueous NaOH and extracted with methylene chloride to give 57.9 g. of product (IV) as an oil. The product was purified via its picrate salt as described in Example 3.

What is claimed is:

1. A compound having the formula

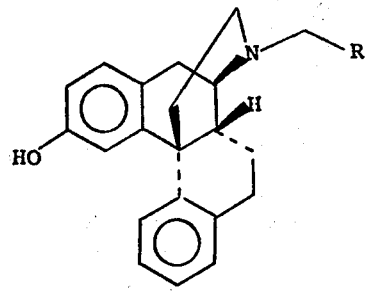

wherein R is selected from the group consisting of

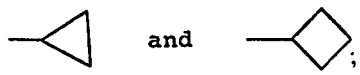

or a pharmaceutically acceptable acid addition salt thereof.

2. A compound as defined in claim 1 wherein R is the group

3. A compound as defined in claim 1 wherein R is the group

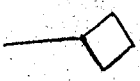

4. The essentially pure levorotatory isomer of the compound of claim 2.

5. The essentially pure dextrorotatory isomer of the compound of claim 2.

6. The essentially pure levorotatory isomer of the compound of claim 3.

7. The essentially pure dextrorotatory isomer of the compound of claim 3.

8. The hydrochloride salt of the compound of claim 2.

9. The hydrochloride salt of the compound of claim 3.

* * * * *